(12) United States Patent
Zhang (10) Patent No.: US 11,097,266 B2
(45) Date of Patent: Aug. 24, 2021

(54) APPARATUS FOR DETECTING THE PRESENCE OR ABSENCE OF AN ANALYTE IN SAMPLES

(71) Applicant: Hangzhou Biotest Biotech Co., LTD., Hangzhou (CN)

(72) Inventor: Kefeng Zhang, Hangzhou (CN)

(73) Assignee: HANGZHOU BIOTEST BIOTECH CO., LTD., Hangzhou (CN)

( * ) Notice: Subject to any disclaimer, the term of this patent is extended or adjusted under 35 U.S.C. 154(b) by 353 days.

(21) Appl. No.: 16/209,293

(22) Filed: Dec. 4, 2018

(65) Prior Publication Data
US 2019/0168208 A1 Jun. 6, 2019

(30) Foreign Application Priority Data

Dec. 6, 2017 (CN) .......................... 201711276092.6
Dec. 6, 2017 (CN) .......................... 201721679827.5

(51) Int. Cl.
*B01L 3/00* (2006.01)
*G01N 33/558* (2006.01)

(52) U.S. Cl.
CPC ............ *B01L 3/502* (2013.01); *G01N 33/558* (2013.01); *B01L 2200/0621* (2013.01); *B01L 2200/143* (2013.01); *B01L 2300/0825* (2013.01); *B01L 2300/0832* (2013.01); *B01L 2300/0858* (2013.01); *B01L 2300/123* (2013.01)

(58) Field of Classification Search
CPC ....... B01L 2200/0621; B01L 2200/143; B01L 2300/0825; B01L 2300/0832; B01L 2300/0858; B01L 2300/123; B01L 3/502; G01N 33/558
See application file for complete search history.

(56) References Cited

U.S. PATENT DOCUMENTS

2013/0004940 A1* 1/2013 Hu ..................... A61B 10/0096
435/5

* cited by examiner

*Primary Examiner* — Jennifer Wecker
*Assistant Examiner* — Jonathan Bortoli
(74) *Attorney, Agent, or Firm* — NZ Carr Law Office (57) ABSTRACT

The present invention provides an apparatus for detecting the presence or absence of an analyte in samples, comprising: a collection chamber for receiving liquid sample, comprising an opening; a testing element for testing the analyte in liquid sample; and a cover body for covering the opening of the collection chamber; wherein the apparatus further comprises a prompting device for prompting if the cover body is covered to a specified location, the prompting device gives prompt by making a sound, wherein the prompting device comprises a non-elastic element and an elastic element, the non-elastic element is located on the collection chamber, the elastic element is located on the cover body, the elastic element is a part of the cover body. It is easy to perform detection using this apparatus, with low processing cost.

18 Claims, 8 Drawing Sheets

APPARATUS FOR DETECTING THE PRESENCE OR ABSENCE OF AN ANALYTE IN SAMPLES

RELATED APPLICATION

The application claims priority to Chinese Application Serial No. 201721679827.5 filed on Dec. 6, 2017 and Chinese Application Serial No. 201711276092.6 filed on Dec. 6, 2017, each of which is herein incorporated in its entirety by reference.

FIELD OF THE INVENTION

The present invention relates to an apparatus for detecting the presence or absence of an analyte in a liquid sample, and in particular, to an apparatus that generates sound to prompt the detection start or completion of covering.

BACKGROUND OF THE INVENTION

It is common to detect body fluids in the medical care fields. Diagnostic testing is increasingly used to maintain the safety of workplaces and ensure compliance with laws, regulations and rules by factories, government agencies, sports teams, etc.

It has become a common method to collect liquid samples (such as urine, etc.) with a detection apparatus and determine the presence or absence of a particular analyte (such as drugs and/or their metabolites, or markers associated with diseases). For such apparatus, samples are usually required to be collected in a sample container, and technicians can insert a test strip and immerse a portion of the test strip in the sample, and subsequently take out the test strip to read the results. Technicians may contact the samples that may endanger their health or contaminate samples. To avoid the risk, it is required to add a closed cover body to the sample collection container before operation. At present, there are a variety of closed devices, for example, the devices disclosed in U.S. Pat. Nos. 4,976,923, 5,429,804, and 6,726,879. The test strips are secured to the lid of the detection apparatus. When used, the container is turned over or tilted to allow the samples to immerse the test strips for testing. The U.S. Patent Application Publication No. US2003/0027359A1 published on Feb. 6, 2003 disclosed a urine cup for detection. For the urine cup for detection, the push rod pushes the piston to move when the cup opening is covered by the lid and make the fluid samples to flow out of the cup chamber and wet the detection element. The Chinese published patent application 200510113977.5 discloses a urine cup for detection. This kind of urine cup can start the liquid to flow from the collection chamber to the detection chamber after the lid is covered to the opening of the cup, to initiate the start of testing. The urine cup starts the testing after the lid is covered to the opening of the cup.

Recently, this detection apparatus has been increasingly used by ordinary families or non-professional organizations. Since these test evaluations are designed for non-professionals, these detection apparatuses should be simple to operate and ensure the accuracy of the test results. At present, the devices that generate sounds to prompt starting or the cover has been covered to a pre-set position are available in the markets. Such detection apparatus has been described in Chinese patents (No. 201110115654.5, No. 200910225108.X and No. 201310582566.5). The apparatus can be operated by operators themselves. When a cover is covered to the opening of a cup body, a mechanical structure will make a sound to prompt operators to stop rotating, to achieve detection more easily, enhance operators' trust and avoid additional problems.

In the Chinese patent 201110115654.5, it is disclosed that a sound is generated by vibration when an elastic piece is deformed and restored to its original shape, and then the vibration is attenuated automatically. In the patents 200910225108.X and 201310582566.5, it is described that an elastic element is deformed after passing through the non-elastic element, and then the cover body is struck in the process of restoring the original state to make a sound. Although the above patents can give a sound, additional structures are required; in addition, it is difficult to operate and produce, especially for disposable plastic product, there are some defects such as high cost of molds, etc.

Therefore, it is urgent to have a kind of detection apparatus with simple operation and accurate and reliable test results. The present invention is to provide a detection apparatus that meets such needs and improve the existing conventional detection apparatus.

SUMMARY OF THE INVENTION

The present invention provides a simple detection apparatus. Specifically, it provides a urinal cup for testing that is easy to operate. When the lid is covered to the opening of the cup, the prompting device on the urine cup will prompt if the lid is covered to the specified location. On the one hand, when the lid is covered to the opening of the cup, the degree of tightness of the lid covered to the opening of cup may vary when operated by different operators especially non-professionals, which may cause unable to seal the opening of the cup and possibility of leakage.

For the present invention, a prompting device is arranged on the detection apparatus, when the lid is covered to the specified location of the collection chamber (the opening of the collection chamber can be adequately sealed by the cover in the location), the prompting device prompts that the opening of the collection chamber is sealed by the lid and operators need not cover the cover again. By this way, the opening of each apparatus can be fully sealed without fear of leakage. On the other hand, in some apparatus, once the lid is closed to the opening of the collection chamber, the liquid sample in the collection chamber will contact with the testing element for testing; at this time, it is required to start to calculate the time, wait for a period of time and read the test results in the detection region of the testing element. When operated by different operators, since the starting time is not consistent, without a unified standard, the test results may be different for different operators. The present invention provides a detection apparatus, and when the lid is covered to the specified location of the collection chamber, the prompting device gives prompt information, such as a sound, to tell the operators the time to wait for the test results from testing element.

On one hand, the present invention provides an apparatus for detecting the presence or absence of an analyte in liquid sample, comprising: a collection chamber, comprising an opening for collecting a liquid sample; and a cover body for covering the opening of the collection chamber; the wherein the apparatus further comprises a prompting device for prompting if the cover body is covered to a specified location.

In some preferred embodiments, when the cover is covered to a specified location, the prompting device prompts that the opening of the collection chamber has been sealed by the cover body. Alternatively, the apparatus further comprises a test element, and the test element is capable of contacting the liquid sample for testing and/or assay of the analyte in the liquid sample. When the cover body is covered to the specified location, the prompting device prompts to calculate the time to wait for the test results from testing element.

In some preferred embodiments, the prompting device gives prompts by making a sound. In some particular embodiments, the prompting device comprises some elements, and these elements can make sound by elastic deformation. Specifically, the prompting device comprises two elements: a first element and a second element. When the first element collides with the second element, one element generates elastic deformations, to rebound and collide with a third element to make a sound to give prompt. In a particular embodiment, the first element is an elastic element, and the second element is a non-elastic element. When the elastic element passes through the non-elastic element, the elastic element is elastically deformed due to compression by the non-elastic element, and when the compression force disappears, the elastic element rebounds to make sound, and the rebound can collide and strike a third element, or the elastic element and the non-elastic element collide each other to make a sound. Here, the third element may be a separate element or an element on a cup body or a cover body, or a part of the structure that constitutes a cup body or a cover body. In some preferred embodiments, the third element is part of the cup body, or a partial area on the cup body corresponding to the first element.

More preferably, the elastic element may be located on the outer surface of the cover edge of the cover body; the non-elastic element may be located on the outer wall surface of the cup mouth. In a more specific embodiment, the elastic element is a portion of the cover edge of the cover body, and the elastic element on the cover edge is a part of the cover body before being deformed but it is coupled to the cover body. Specifically, in order to dispose the elastic element on the cover body, a part of the cover edge is separated as an elastic element, and usually an internal thread structure is provided in the cover edge, and there is a spacing between the partitioned portion and other portion of the cover edge, usually 1-2 mm in width, or, there are spacing between both sides of the partitioned portion and the other portion of the cover edge, and one side is connected to the cover edge. For example, the partitioned portion (the elastic element itself) is approximately 1/20 of the cover edge, or smaller, and generally it is rectangular. The long side of the partitioned portion on the cover edge is separated from the cover edge, while the short side is connected to the cover body, and another short side is exposed as the side of the cover edge of the cover body, which is called an exposed side. Such a structure can generally be achieved by injection molding a disposable mold. For example, when the cover body is injection-molded, the mold has a structure corresponding to the cover body, and the cover body, for example, a partial cover edge, is formed by one-time injection molding with a spacing arrangement. For such a relatively conventional structure, it is still a cover body from the outer appearance, and no redundant structure protrudes from the outer surface, while the elastic element is hidden on the cover body. It will be described on how to make a sound below.

Preferably, a non-elastic element is disposed on the cup body, the non-elastic element is substantially parallel to the longitudinal direction of the cup body, but the non-elastic element is slightly inclined toward the cup body, such that the protruding end or the exposed end of the non-elastic element is in contact with the inner side or inner surface of the exposed side of the elastic element on the cover body when the cup mouth is covered by the cover body. When the cover body rotates to cover the cup mouth, the non-elastic element continues to contact with the inner side of the exposed side of the elastic element on the cover body. As the elastic element is almost not deformed, the elastic element on the cover body is subject to a pushing force outwards, which is naturally protruded out of the cover of the cover body, or warped. The elastic element is generally rectangular, and the longer two sides have space from the cover edge, to warp along the circumference of the other portion of the cover edge. When the non-elastic element is disengaged from the elastic element (as the relative position changes), the elastic element needs to return to the original position, to strike the cup body and make a sound.

In some more preferred embodiments, an inelastic element or a protrusive structure is provided on the outer surface or/and the inner surface of the exposed side of the elastic element on the cover edge, and the non-elastic element may be located above the exposed side of the elastic element, or a part of the exposed side of the elastic element is a non-elastic material, such that the non-elastic element on the cup body is in contact with the non-elastic part of the elastic element, which makes it easier to denature the elastic element.

In a preferred embodiment, a convex non-elastic element is provided on the exposed side of the elastic element, and the non-elastic element on the elastic element is in contact with the non-elastic element on the cup body, such that the elastic element is easier to bulge or upwarp towards the surface where the cover edge is located, to generate deformation. Preferably, the underside of the non-elastic element on the elastic element is in contact with the top end of the non-elastic element on the cup body, such that the elastic element is easier to bulge or upwarp towards the surface where the cover edge is located.

In addition, the non-elastic element and the collection chamber can move counterclockwise relative to the cover body; the elastic element and the cover body can move clockwise in synchronization relative to the collection chamber. In an alternative solution, the elastic element is elastically deformed under the interaction force of the elastic element on the cover body and the non-elastic element on the cup body. When the interaction force disappears, the elastic element and the non-elastic element on the cup body collide with each other to make a prompting sound.

In other particular embodiments, the non-elastic element is composed of an ABS material; the elastic element is composed of a PP material. Alternatively, after the elastic element passes through the non-elastic element to tap the cup body, the elastic element is blocked by the non-elastic element so as not to move clockwise relative to the cup body. In another optional embodiment, after the elastic element passes through the non-elastic element to tap the cup body, the elastic element can move clockwise relative to the cover body. Optionally, the cover body covers the opening of the collection chamber in such a manner that the cover body seals the opening of the collection chamber by means of rotation. The opening comprises an external thread that fits the cover body, and the cover body comprises an internal thread that fits the opening.

In some preferred embodiments, the elastic element on the cover edge does not have an internal thread that fit the outer thread of the cup body.

In another aspect, the present invention provides a method of detecting analyte in a sample, comprising providing a detection apparatus, comprising: a collection chamber comprising an opening for collecting a liquid sample, and a cover body for covering the opening of the collection chamber; The cover is covered to the opening of the collection chamber and one prompting device on detection apparatus prompts whether the cover body is closed to the specified location. In one way, the prompting device prompts by making a sound. In another way, once you hear the prompting device to give a prompt, stop continuing to cover the cover to the collection chamber's opening. In a specific way, the cover closes the opening of the collection chamber in a rotation way, and when you hear the prompting device, it is prompted to stop the cover body. In addition, in a way, once you hear the prompting device to give a prompt, start calculating the time to wait for the test results from testing element. In another way, once you hear the prompting device to give a prompt, start calculating the time to wait for the test results from testing element, and stop rotating the cover body.

The present invention provides a method for detecting analyte in a sample comprising: providing a detection apparatus comprising a collection chamber containing an opening; a testing element; and a cover body for sealing the opening of the collection chamber through rotation relative to collection chamber, wherein the apparatus furthers comprises a prompting device that prompts whether the cover body is rotated to the specified location; rotating the cover body until the prompting device gives prompt.

In some preferred embodiments, the rotation is stopped when the prompting device gives a prompt. Optionally, when the prompting device gives a prompt, it begins to calculate the time required to wait for the detection result read from the testing element. In a particular embodiment, the prompting device gives prompt by making a sound. More preferably, the prompting device comprises a non-elastic element protruding from the outer surface of the collection chamber and an elastic element on the cover edge, the elastic element being part of the cover edge of the cover body. During the rotation of the cover body, the elastic element is deformed after pressing an exposed side of the non-elastic element. When the non-elastic element is detached from the elastic element, the non-elastic element strikes the cup body to make a sound. Most preferably, the non-elastic element comprises a protrusive structure having certain rigidity, and the exposed side of the elastic element as a part of the cover edge of the cover body is in contact with the protrusive structure of the non-elastic element to upwarp outwards.

Beneficial Effects

The apparatus and method of the present invention make it easier to operate, suitable for non-professionals; and the detection results are more accurate. In addition, the apparatus is inexpensive, easy to operate, and can make a crisp sound easily.

BRIEF DESCRIPTION OF THE DRAWINGS

FIG. 8A-FIG. 8C is a structural diagram of a process in which a cover body is covered to a cup body.

DETAILED DESCRIPTION

The structure referred to in the present invention or the technical terms used therein will be further described below.

Detection

Detection means to assay or test the presence or absence of a substance or material, including but not limited to chemical substances, organic compounds, inorganic compounds, metabolic products, medicines or drug metabolites, organic tissues or metabolites of organic tissues, nucleic acids, proteins or polymers. Additionally, detection means to test the quantity of a substance or material. Furthermore, assay also means immunodetection, chemical detection, enzyme detection, etc.

Detection Apparatus

In a specific embodiment, the detection apparatus comprises a collection chamber 10 used to collect and store liquid samples, the collection chamber is enclosed by a side wall 101 and a base, comprising an opening 101 for leading in liquid samples. "A or an" said in the description of this invention including abstract and claims should be interpreted as at least one, or comprising one in quantity, and should not be understood as "unique" or "only one". For example, the detection apparatus comprises a prompting device, obviously meaning that the description that the detection apparatus comprises two or more prompting devices should also fall into the scope of the claims of this invention and should not be excluded. The detection apparatus can also comprise a detection chamber 207, and the detection chamber comprises a testing element, and the liquid sample in the collection chamber can contact with the testing element in the detection chamber freely or under control; and the chemical reagent on the testing element can test the presence or absence of, or the quantity of analyte in liquid sample. The detection apparatus can also comprise a cover body 30, which is used to cover the opening 100 of the collection chamber. In a specific way, the detection apparatus comprises a prompting device, which can prompt if the cover body is covered to a specified location, particularly, to a specified location on the collection chamber. On the one hand, when the cover body is covered to the specified location of the collection chamber, the prompting device can prompt that the opening of the collection chamber has been sealed by the cover body. On the other hand, when the cover body is covered to the specified location of the collection chamber, the prompting device can prompt to start to calculate the time needed to wait for reading the test results from the testing element. There are many ways to cover the cover body to the collection chamber, such as in the form of thread. For example, the opening of the collection chamber comprises the external thread, and the cover body comprises the internal thread matching with the external thread; after the cover body is covered to the collection chamber, the opening is sealed through relative rotation, and moreover, the opening can be sealed by inserting the cover body into the opening in a form of piston.

The prompting device provided in this invention can also be applied to other detection apparatuses, particularly, to those apparatuses containing cover and using cover to seal the opening of the collection chamber. These similar apparatuses are described specifically in US patents that have been published such as U.S. Pat. Nos. 7,270,959; 7,300,633; 7,560,272; 7,438,852; 4,976,923; 5,429,804 and 6,726,879. The prompting device disclosed in this invention can be combined to the specific ways of each detection apparatus disclosed in the above patents as one of the specific ways of this invention.

Prompting Device

In a specific way, the prompting device can be arranged on the detection apparatus. The prompting device gives prompts by making a "Pa", "Peng", "Dong", "Dingling", "Pipa" sound or any other suitable sounds.

The prompting device generally comprises elements: an elastic element and a non-elastic element. The "elastic element" and "non-elastic element" as used herein are relative concepts. In terms of setting, in general, the elastic modulus of the elastic element is smaller than the elastic modulus of the non-elastic element. For example, plastic is used as the elastic element, and metal such as iron, steel or lead, is used as the material of the non-elastic element, so that elastic modulus of the elastic element is smaller than that of the non-elastic element under the interacting force of the plastic and the non-elastic element. When the interacting force between them is the same, the elastic element is relatively easy to change shape, and when the force disappears instantaneously, the elastic element needs to be restored to the original shape, to strike the third element (or the cup body) or strike the second element to generate vibration and make a sound. The force for generating elastic deformation is usually smaller than the inherent elastic limit of the element, so that they can restore the original shape automatically after the external force disappears. Optionally, both the elastic element and the non-elastic element are made of plastic materials.

In some preferred embodiments, for example the structure shown in FIGS. 1A-1D, the elastic element 31 is located on the cover body as part of the cover body, in particular, as a part of the cover edge 30. The inside of the cover edge includes the internal thread and the opening of the cup body that cooperates with the external thread of the cup body to rotate and seal the cup body. The elastic element may have an internal thread or have no internal thread. The elastic element 31 is roughly a rectangular shape, and the two long sides have a partition with the other longitudinal portions 32, 35 of the cover edge 30 such that one short side is connected to the cover edge and the other short side is suspended as an exposed side and also a side of the cover edge. When the non-elastic element 33 on the cup body passes through the elastic element, since the non-elastic element is in contact with the one side (inner surface) 36 of the elastic element close to the cup body (FIG. 1B), the elastic element will have a deformation from the inside to the outside with the movement of relative position. As the elastic element is subjected to an outward force along the cover edge plane, it protrudes from the circumferential plane of the cover edge (FIG. 1C), to generate an upwarp deformation. When the elastic element 31 is detached from the non-elastic element 33, the deformed elastic element 31 restores to original shape and strike the cup body structure, to make a sound. The structure that strikes the cup body is a part of the cup body, for example, a part of buckled structure corresponding to the elastic element. In such a structure, in order to allow the non-elastic element 33 to smoothly contact the back surface of the elastic element 31, when the cover body is covered to the opening of the cup, the elastic element 31 and the cover edge 30 are substantially in the same circumferential plane, and the elastic element 31 can block the contact with the back surface 36 of the elastic element. When setting the non-elastic element 33, the non-elastic element 31 is slightly tilted toward the inner side of the cup body, and when the cover body is covered to an appropriate location, the top end of the non-elastic element 33 passes through the blocked opening (entering from the opening) to contact the back surface 36 of the elastic element 31, thereby deforming the elastic element 31.

A part of the cover edge of the cover body is used as an elastic element, which is easier to achieve than addition of structure to the cover edge in the conventional technology, and it has a lower manufacturing cost, since the mold processing is simpler. For example, in the patents 200910225108.X and 201310582566.5, a non-elastic element (a gradually increased step) is added to the cover edge, and an elastic element is provided on the cup body. The elastic element is deformed when passing through the non-elastic element, to strike the cover body to make a sound. It is required to provide a non-elastic element on the cover body. Usually a non-elastic element and cover edge should be made of the same material, so the cover body should be made of a rigid material or the cover edge should be thick to deform the elastic element relative to the cup body, which will increase the cost. In addition, during operation, the cover body is generally used to cover the cup mouth of the cup body, so that the elastic element on the cover body is in contact with the non-elastic element on the cup cover. The non-elastic element is in a shape of a gradual increased step, which requires a great force. It needs to deform the elastic element and overcome the friction between them. It is not easy to operate for a person with small hand strength. In the present invention, a part of the cover body is used as an elastic element, which saves the cost and reduces the operability difficulty; in addition, it is hidden, so the product has better operating performance.

In the present invention, a part of the cover body is used an elastic element and the elastic element itself is deformed. When the elastic element is restored to its original position after deformation, it strikes the cup body or other non-elastic element to make a sound, so part of the cover body needs to be deformed. The cover edge of the cover body needs not to be thick, and it can be achieved by a thin cover edge, saving materials. Its cost is low as a disposable item. In addition, in terms of operability, a part of the cover edge is used as an elastic element, and the elastic element is easier to deform during rotation, for example, one end of the elastic element is in contact with the non-elastic element, such that the elastic element is deformed. Once the non-elastic element is detached from one end of the elastic element, the elastic element restores to its original state, to strike the cup body and make a sound. In addition, since the cover body is made of a relatively soft material, the non-elastic material is made of a slightly hard material, with low cost. It is easy for the non-elastic material to enter the inner surface of the elastic element through the gap; with the movement of the position, it will exert an outward force to the elastic element to generate deformation.

Figure 1A:
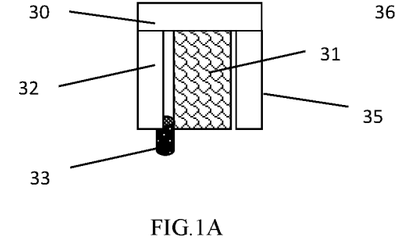
FIG. 1A-FIG. 1D is a schematic structural diagram of sounding in a specific embodiment of the present invention.
Figure 1B:
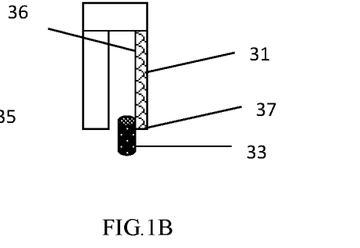
Figure 1C:
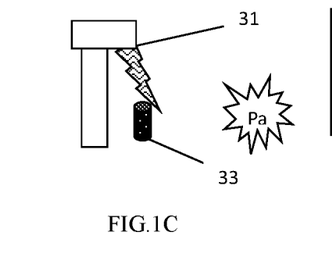
Figure 1D:
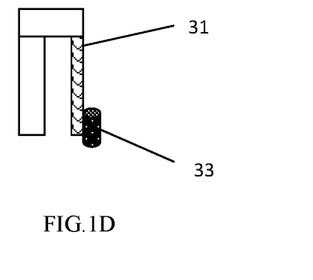
Figure 2A:
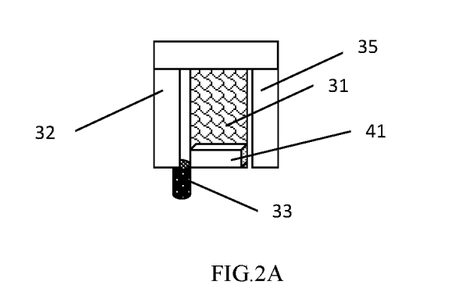
FIG. 2A-FIG. 2D is a schematic structural diagram of sounding in another specific embodiment of the present invention.
Figure 2B:
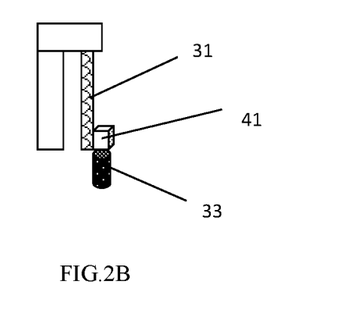
Figure 2C:
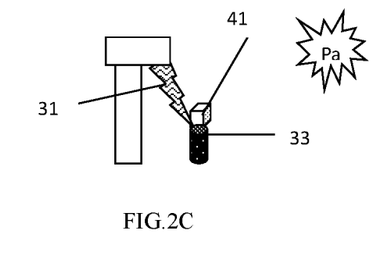
Figure 2D:
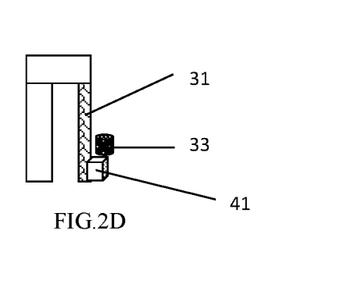

In other embodiments, a second non-elastic element (a rigid protrusion, or a protrusive structure) is provided on the exposed end of the elastic element, to facilitate the non-elastic element on the cup body to contact with the elastic element, and facilitate the deformation of the elastic element. For example, as illustrated in FIGS. 2A-2D, its difference from that illustrated in FIGS. 1A-1D is that the outer surface on the exposed end of the elastic element 31 comprises a second non-elastic element, and the second non-elastic element may be naturally thickened at one end of the elastic element 31. With the increase in thickness, it protrudes relative to the circumferential plane of the cover edge. By this way, the non-elastic element 33 on the cup body needs not setting of the position and shape as shown in the FIGS. 1A-1D (allowing the top end of the non-elastic element 33 to incline inwardly), but it needs to be located on the same position of the plane of the cover edge, but not in the same plane as the protruding element 41. When non-elastic element passes through the elastic element, the non-elastic element 33 is in contact with the protrusive structure 41 due to the setting of the protrusive structure 41, so that the surface of the protrusive structure 41 is in contact with the non-elastic element 33. As the protrusive rigid structure 41 is located at one end of the elastic element 31, deformations such as outward bulging and upwarp occur easily for the elastic element. With the movement of their positions and subsequent detachment, the deformed element 31 restores its original shape and strikes a third element (for example, the cup body itself) to make a sound. Compared to the structure in the FIG. 1 of the embodiment, the structure in this embodiment needs not additionally design the shape and the position of the non-elastic element, but the protrusive structure on the elastic element 31 is required to contact with the non-elastic element. This contact can allow the non-elastic element to apply an outward force to the protrusive structure, to allow the elastic element to produce outward deformation (FIG. 2C). To apply an outward force to the protrusive structure, the top end of the non-elastic element may be in contact with the protruding element 41, or in contact with the protruding element (41) in a transverse section way. The protruding element herein is a relatively rigid material, or is not easily deformed relative to the elastic element. Of course, if the size and thickness are different just like the elastic element 31, for example, by thickening the $\frac{1}{10}$ outer surface at one end of the elastic element 31, it can achieve such effect.

Figure 3A:
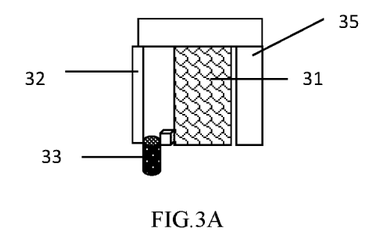
FIG. 3A-FIG. 3D is a schematic structural diagram of sounding in another specific embodiment of the present invention.
Figure 3B:
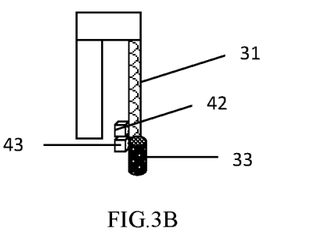
Figure 3C:
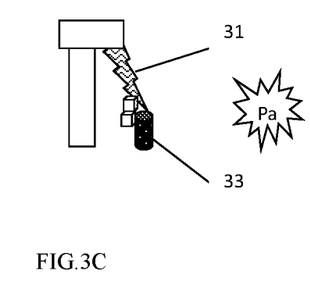
Figure 3D:
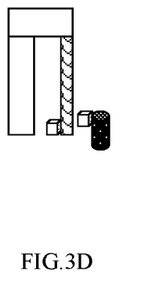

In some other embodiments, a non-elastic element (a rigid protrusion) is provided on the exposed end of the elastic element, to facilitate the non-elastic element on the cup body to contact with the elastic element, and facilitate the deformation of the elastic element. For example, as illustrated in FIGS. 3A-3D, its difference from that illustrated in FIGS. 2A-2D is that the outer surface on the exposed end of the elastic element 31 comprises a second non-elastic element 42 or a protruding element, and the second non-elastic element 42 may be naturally thickened at one end of the elastic element 31. With the increase in thickness, it protrudes relative to the circumferential plane of the cover edge. By this way, the non-elastic element 33 on the cup body needs not setting of the position and shape as shown in the FIGS. 2A-2D, but it needs to be located on the same position of the plane of the cover edge, but not in the same plane as the protruding element 42. When non-elastic element passes through the elastic element, the non-elastic element 33 is in contact with the protrusive structure 42 due to the setting of the protrusive structure 42, so that the surface of the protrusive structure 42 is in contact with the non-elastic element 33. As the protrusive rigid structure 42 is located at one end of the elastic element 31, deformations such as outward bulging and upwarp occur easily for the elastic element. With the movement of their positions and subsequent detachment, the deformed element 31 restores its original shape and strikes a third element (for example, the cup body itself) to make a sound. Compared to the structure in the FIG. 1 of the embodiment, the structure in this embodiment needs not additionally design the shape and the position of the non-elastic element, but the protrusive structure on the elastic element 31 is required to contact with the non-elastic element. This contact can allow the non-elastic element to apply an outward force to the protrusive structure, to allow the elastic element to produce outward deformation (FIG. 3C). To apply an outward force to the protrusive structure, the top end of the non-elastic element may be in contact with the protruding element 42, or in contact with the protruding element (42) in a transverse section way. The protruding element herein is a relatively rigid material, or is not easily deformed relative to the elastic element. Of course, if the size and thickness are different just like the elastic element 31, for example, by thickening the $\frac{1}{10}$ outer surface at one end of the elastic element 31, it can achieve such effect. More preferably, a protrusion 43 is provided at one end of the non-elastic element 33, and the protrusive structure 43 is in contact with the protrusive structure 42 of the inner surface of the elastic element 31, to apply an outward force to the protrusive structure 42, so that outward deformation of the elastic element occurs. When the force disappears, the elastic element 31 rebounds to strike the cup body and make a sound. The material of protrusive structure 42 of the non-elastic element 33 may be the same as or different from that of the non-elastic element 33, which can be set and selected according to the appropriate material.

Figure 4:
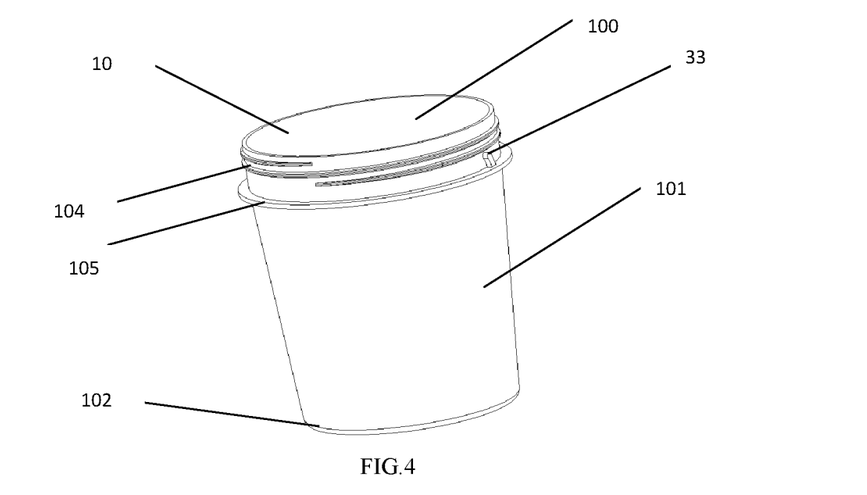
FIG. 4 is a schematic view of a three-dimensional structure of a cup body in which a non-elastic element is located on a cup body in a specific embodiment of the present invention.

In another embodiment, the present invention provides a cup body, as shown in FIG. 4, comprising a chamber for collecting fluid samples. The chamber is enclosed by a side wall 101 and a base 102. The collection chamber has an opening 100. A cup edge 104 is provided at the opening. The cup edge has a thread that matches with the internal thread of the cover body to cover the opening of the collection chamber. A cup edge 105 is provided below the thread of the collection chamber, and the cup edge is an annular protrusion structure on which a non-elastic element 200 is disposed.

Figure 5:
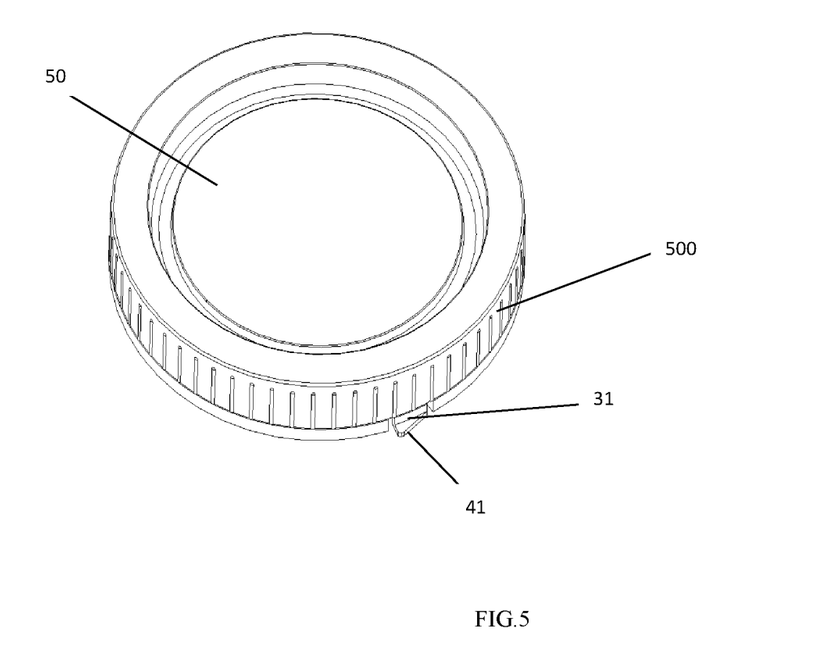
FIG. 5 is a schematic view of a three-dimensional structure of a cover body in which an elastic element is located on the cover body and is a part of a cover edge in a specific embodiment of the present invention.
Figure 6:
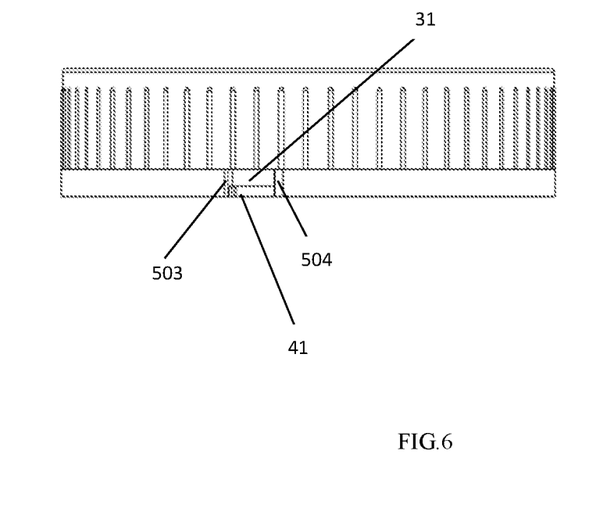
FIG. 6 is a drawing of a cover edge surface of a cover body with an elastic element in a specific embodiment of the present invention (a cover body in FIG. 5).
Figure 7:
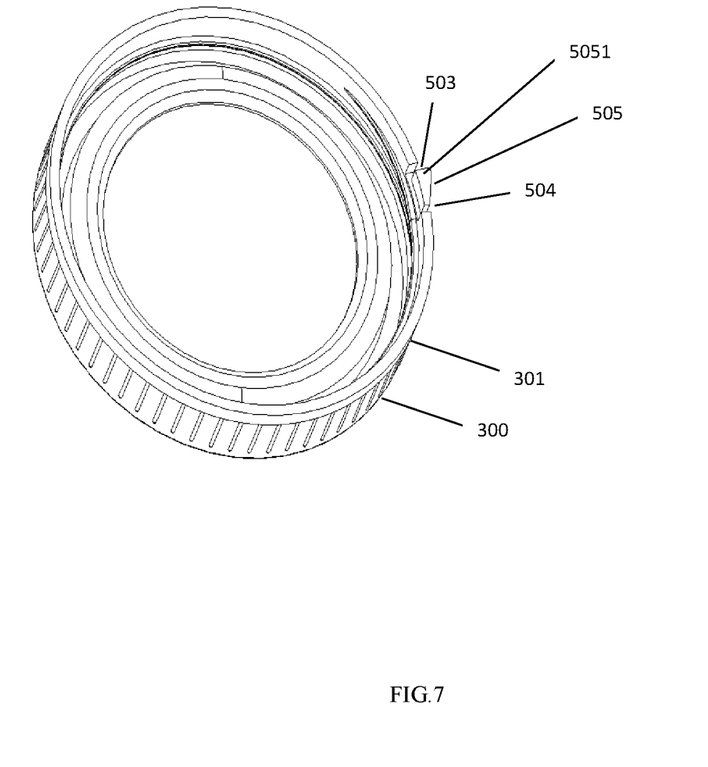
FIG. 7 is a schematic view of a three-dimensional structure of a cover edge surface of a cover body with an elastic element in a specific embodiment of the present invention (a cover body in FIG. 5).

The present invention provides a cover body 50, comprising a cover edge 500. An elastic element is disposed on the cover edge 500. The elastic element is a part of the cover body, and the elastic element 502 is separated from other parts of the cover body as an elastic element, as shown in FIGS. 5 and 6. There is a partition or a gap 503, 504 between the elastic element and other portions of the cover edge. The partition may be a gap of 1-2 mm, 1 mm, 2 mm, 3 mm, 4 mm, 5 mm. Moreover, a protruding element 505 is disposed at the outside of one end of the elastic element. The protruding element is located on the outer surface of the elastic element, and the protruding element may be in a trapezoidal shape, or other shapes. The protrusive structure 505 is protruded toward the outer surface 300 of the cover body, as shown in FIG. 7. The protrusive structure is located outside the elastic element and protrudes laterally outward, while the protruded surface 5051 and the cover edge 301 of the cover body are in the same plane. By this way, the cover body is easily in contact with the non-elastic element when the cup is covered.

Figure 8A:
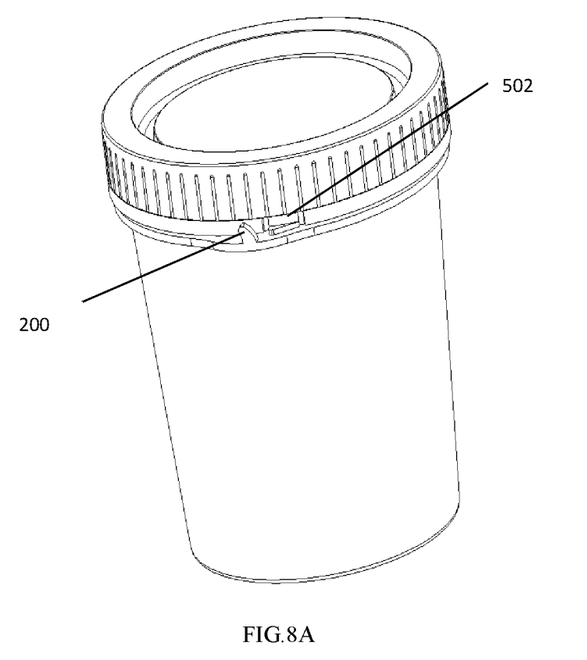
FIG. 8A shows a structural diagram of a contact when a cover body covers a cup body.
Figure 8B:
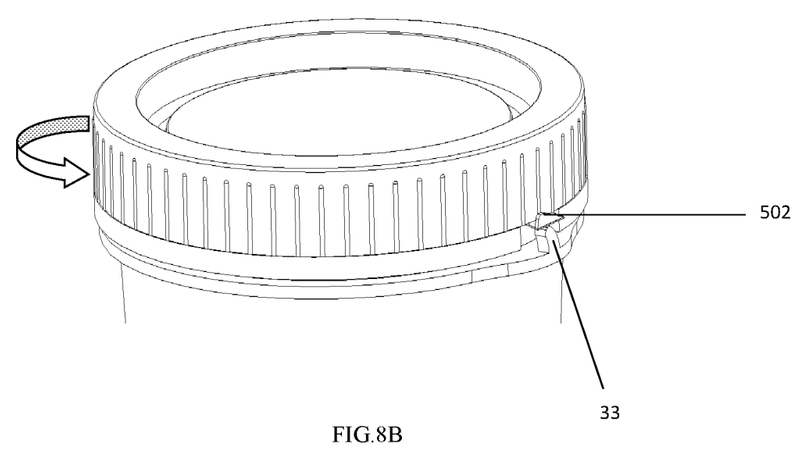
FIG. 8B shows a structural diagram of an elastic element is upwarped towards the periphery of the cover edge when subjected to a force.
Figure 8C:
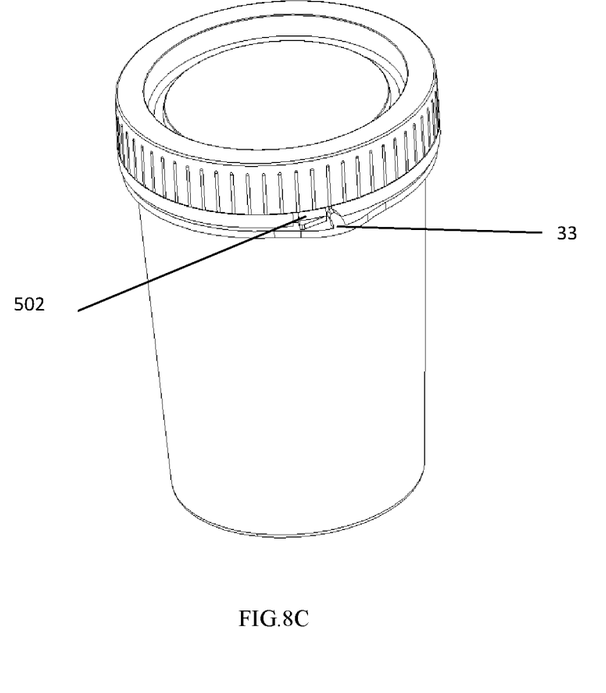
FIG. 8C shows a schematic diagram of the positional relationship after the non-elastic element and the elastic element are separated.

When the cover body is covered to the opening of the collection chamber, the internal thread in the cover body matches with the external thread of the collection chamber, to achieve covering by relative rotation. As the rotation progresses, the non-elastic element 200 is gradually close to and contacts with the elastic element (as shown in FIG. 8A). When the non-elastic element 200 is in contact with the protrusive structure 505 on the outer surface of the elastic element or at the intersection between the protrusive structure 505 and the elastic element, the elastic element is easily subject to an outward force due to the interaction each other. Under the same force, the elastic element is prone to deformation, as shown in FIG. 8B. At this time, the elastic element is deformed outwardly. When they are not in contact with each other, the interaction force disappears, the elastic element 502 needs to restore the original shape to strike the cup body, specifically to strike the cup edge or the external thread on the cup body, to make a sound, as shown in FIG. 8C. The striking place is the location on the elastic element corresponding to the cup body. As the rotation speed is relatively fast, it will make a crisp and clear sound, prompting that the cover is covered to the specified location.

In addition, the principle structure shown in FIGS. 1-3 can also be applied to specific products appropriately. For example, a non-elastic element is located on a cup body as shown in FIG. 4, an elastic element and other structures are located on the cover body as shown in FIG. 5. This can be readily accomplished by ordinary technicians skilled in the art after reading the present invention.

Detection Method

The present invention provides a method for detecting analyte in a sample, comprising providing a detection apparatus, comprising: a collection chamber comprising an opening for collecting a liquid sample, a testing element for testing the analyte in liquid sample; and a cover body for covering the opening of the collection chamber; covering the lid to the opening of the collection chamber, so that one prompting device on the detection apparatus can prompt if the cover body is covered to the specified location. In one way, the prompting device gives prompts by making a sound. In another way, once you hear the prompting device to give a prompt, stop covering the cover body to the opening of the collection chamber. In a specific way, the cover body closes the opening of the collection chamber by rotating; and when hearing prompt given by the prompting device, you can stop rotating the cover body. In addition, in a way, once you hear a prompt given by the prompting device, start calculating the time to wait for the test results from testing element. In another way, once you hear a prompt given by the prompting device, start calculating the time to wait for the test results from testing element, and stop rotating the cover body.

Testing Element

The testing element may be a lateral flow test strip that can be used to detect multiple analytes. Of course, other appropriate testing elements can also be used in the present invention.

Various testing elements can be combined and applied to the present invention. One form is the test strip. The test strip used to analyze the analyte in the sample (such as drugs or metabolites indicating physical condition) may be in various forms, such as immunoassays or chemical assays. The test strip can be analyzed by non-competitive or competitive methods. The test strip comprises a water absorbing material with a sample applying zone, a reagent zone and a testing zone. Samples are added to the sample applying zone, and flowed to the reagent zone by capillary action. In the reagent zone, if an analyte is present, the sample is bound with the reagent, and then the sample continues to flow to the testing zone. Other reagents, such as molecules that specifically bind to the analyte, are immobilized in the testing zone. These reagents react with the analyte in the sample (if present) and bind the analyte to the zone, or bind to a reagent in the reagent zone. The markers used to display the detection signals are present in the reagent zone or a separate mark zone.

A typical non-competitive method of analysis is that signals will be generated if the samples contain analytes, and no signals will be generated if the samples do not contain analytes. In the competitive method, if the analyte is not present in the sample, the signal is generated, and if the analyte is present in the sample, no signal is generated.

The testing element is a test strip, which can be made of water-absorbent or non-absorbent material. The test strip may contain a variety of materials for delivery of liquid samples. One material of a test strip can be covered to another material, for example, a filter paper is covered to a nitrocellulose membrane. One zone of the test strip may adopt one or more materials, and the other zone may adopt one or more different materials. The test strip can be attached to a support or a rigid surface to increase the strength of the test strip.

The analyte is detected by a signal generation system. For example, by using one or more enzymes that specifically react with the analyte and the foregoing method of immobilizing the specific binding substance on the test strip, the composition of one or more signal generation systems is immobilized on the analyte testing zone of the test strip. The substance that generates signals may be in the sample applying zone, reagent zone, or testing zone, or the entire test strip, which can be filled with one or more materials of the test strip. The solution containing the signal is applied to the surface of the test paper or one or more materials of the test paper are immersed in the signal-containing solution. The test paper added with the signal containing solution is dried.

The zones of the test strip can be arranged in the following sequence: a sample applying zone, a reagent zone, a testing zone and a control zone, a sample adulteration zone, a liquid sample absorption zone. The control zone is located after the testing zone. All zones can be arranged on a test strip of the same material, or different zones adopt different materials. Each zone may be in direct contact with the liquid sample, or different zones may be arranged in the direction in which the liquid sample flows, and the end of a zone is connected to and overlapped with the front end of the other zone. The material used may be a material having good water absorption such as filter paper, glass fiber or nitrocellulose membrane, etc. The test strip may be in other forms.

Type of Samples

Any type of sample, including body fluids (e.g., urine and other body fluids, as well as clinical samples), can be tested using the apparatus in the present invention. Liquid samples may be derived from solid or semi-solid samples, including feces, biological tissues, and food samples. These solid and semi-solid samples can be converted to liquid samples by any suitable method, for example, mixing, mashing, macerating, incubating, dissolving or enzymatically dissolving solid samples (e.g., water, phosphate buffer or other buffer)

in a suitable liquid. "Biological samples" include samples derived from living animals, plants and food, as well as urine, saliva, blood and blood components, cerebrospinal fluid, vaginal swabs, semen, feces, sweat, secretions, tissues, organs, tumors, cultures of tissues and organs, cell cultures and conditional media from human or animals. Food samples comprise food processed substances, final products, meat, cheese, liquor, milk and drinking water. Plant samples comprise samples from any plants, plant tissues, plant cell cultures and media. "Environmental samples" come from the environment (such as liquid samples coming from lake or other water bodies, sewage samples, soil samples, underground water, sea water and effluent samples), and can also comprise waste water or other wastes.

Type of Analytes

Any analyte can be analyzed by the present invention. Examples of analytes that can be stably detected using the present invention include, but not limited to, human chorionic gonadotropin (hCG), luteinizing hormone (LH), ovarian stimulating hormone (FSH), hepatitis C virus (HCV), hepatitis B virus (HBV), hepatitis B surface antigen, HIV and any drugs of abuse. The analyte can be detected in any liquid or liquefied sample, such as urine, saliva, blood, plasma, or serum. Examples of other analytes include creatinine, bilirubin, nitrite, protein (non-specific), blood, white blood cells, blood sugar, heavy metals and toxins, bacterial components (e.g., specific proteins and sugars of certain types of bacteria, such as *E. coli* 0157:H7, *Staphylococcus aureus, Salmonella, Clostridium perfringens, Campylobacter, Listeria monocytogenes, Vibrio parahaemolyticus*, or *Bacillus cereus*). Any other analyte suitable for the lateral flow test can be detected by the apparatus. The analyte may also be an infectious substance or a substance that may indicate an infection period. The analyte can be a drug (such as a drug of abuse), a hormone, a protein, a nucleic acid molecule, or a pathogen. "Drug of Abuse" (DOA) refers to the use of drugs in non-medical purposes (usually for the role of nerve paralysis). Abuse of these drugs can cause physical and mental damage, generate dependence, addiction and/or death. Examples of drug abuse include cocaine; amphetamines (e.g., Black Beauty, white amphetamine tablets, dextroamphetamine, dextroamphetamine tablets, Beans); methamphetamine (crank, methamphetamine, crystal, speed); barbiturates (e.g., Valium®, Roche Pharmaceuticals, Nutley, N.J.); sedatives (i.e., sleeping adjuvants); lysergic acid diethylamide (LSD); inhibitors (downers, goofballs, barbs, blue devils, yellow jackets, methaqualone); tricyclic antidepressants (TCA, i.e. imipramine, amitriptyline and doxepin); phenylcyclohexyl piperidine (PCP); tetrahydrocannabinol (THC, Pot, dope, hash, weed, etc.); opiates (i.e., morphine, opium, codeine, heroin, oxycodone). The test strip can also be used for tests that are medically useful but are easy to overdose, such as tricyclic antidepressants (imipramine or analogues) and acetaminophen.

All patents and publications mentioned in the specification of the present invention are disclosures of the prior art and they can be used in the present invention. All patents and publications referred to herein are incorporated in the references as if each individual publication is specifically referred to separately. The invention described herein may be practiced in the absence of any one or more of the elements, any one limitation or more limitations that are not specifically recited herein. For example, the terms "comprising," "consisting essentially of," and "consisting of" in each instance herein may be replaced with each of the remaining two terms. The term "a(an) . . . " as used herein merely means "a(an) . . . ", which does not mean only "one", but may mean "two or more". The terms and expressions which have been employed herein are descriptive rather than restrictive, and there is no intention to suggest that these terms and expressions in this description exclude any equivalents, but it is to be understood that any appropriate changes or modifications can be made within the scope of the present invention and appended claims. It should be understood that, the embodiments described in the present invention are some preferred embodiments and features, and any person skilled in the art may make some changes and variations based on the essence of the description of the present invention, and these changes and variations are also considered to fall into the scope of the present invention and the independent claims and the appended claims.

The invention claimed is:

1. An apparatus for detecting an analyte in a liquid sample, comprising a collection chamber for receiving the liquid sample, comprising an opening; a testing element for testing the analyte in the liquid sample; and a cover body for covering the opening of the collection chamber; wherein the apparatus further comprises a prompting device for prompting if the cover body is covered to a specified location, the prompting device gives prompt by making a sound, wherein the prompting device comprises a non-elastic element and an elastic element, the non-elastic element is located on a cup body of the collection chamber, the elastic element is located on the cover body, wherein the cover body comprises a cover edge, wherein the elastic element is part of the cover body, and wherein the elastic element is a partitioned portion of the cover edge separated from a remaining portion of the cover edge by two gaps.

2. The apparatus according to claim 1, wherein the elastic element is a rectangular structure including two long sides and two short sides, the two long sides of the rectangular structure being adjacent to each of the two gaps of the cover edge of the cover body, and wherein a first short side of the two short sides is connected to the cover edge and a second short side of the two short sides is exposed.

3. The apparatus according to claim 2, wherein the inner surface of the elastic element on the exposed short side has a protrusive structure.

4. The apparatus according to claim 2, wherein the outer surface of the elastic element on the exposed short side has a protrusive structure.

5. The apparatus according to claim 3, wherein the protrusive structure has the same material as the elastic element, and the thickness of the protrusive structure is greater than that of the elastic element.

6. The apparatus according to claim 4, wherein the elastic modulus of the protrusive structure is greater than the elastic modulus of the elastic element.

7. The apparatus according to claim 3, wherein the non-elastic element is provided on an outer wall of the collection chamber, during the rotation and covering of the external thread of the collection chamber and the internal thread of the cover body, the non-elastic element contacts the protrusive structure on the inner surface of the elastic element to move relative to each other, to allow the elastic element to deform.

8. The apparatus according to claim 4, wherein the non-elastic element is provided on an outer wall of the collection chamber, during the rotation and covering of the external thread of the collection chamber and the internal thread of the cover body, the non-elastic element contacts the protrusive structure on the outer surface of the elastic element, to allow the elastic element to deform.

9. The apparatus according to claim 1, wherein the collection chamber has an external thread, and the cover body has an internal thread cooperating therewith, and the elastic element on the cover body does not have an internal thread.

10. The apparatus according to claim 7, wherein the direction of deformation is away from the circumferential plane where the cover edge is located.

11. The apparatus according to claim 8, wherein the direction of deformation is away from the circumferential plane where the cover edge is located.

12. The apparatus according to claim 7, wherein the elastic element rebounds to strike the cup body to make a sound from the non-elastic element contacts the protrusive structure on the inner surface of the elastic element until the non-elastic element does not contact the protrusive structure on the inner surface of the elastic element.

13. The apparatus according to claim 8, wherein the elastic element rebounds to strike the cup body to make a sound from the non-elastic element contacts the protrusive structure on the outer surface of the elastic element until the non-elastic element does not contact the protrusive structure on the outer surface of the elastic element.

14. The apparatus according to claim 12, wherein the elastic element rebounds to strike the cup edge portion opposite to the elastic element to make a sound from the non-elastic element contacts the protrusive structure on the inner surface of the elastic element until the non-elastic element does not contact the protrusive structure on the inner surface of the elastic element.

15. The apparatus according to claim 13, wherein the elastic element rebounds to strike the cup edge portion opposite to the elastic element to make a sound from the non-elastic element contacts the protrusive structure on the outer surface of the elastic element until the non-elastic element does not contact the protrusive structure on the outer surface of the elastic element.

16. The apparatus according to claim 1, wherein the testing element is a drug testing element.

17. The apparatus according to claim 16, wherein the testing element is a lateral flow test strip.

18. The apparatus according to claim 17, wherein the lateral flow test strip is an immunoassay strip.

* * * * *